United States Patent [19]

Lind

[11] 4,021,468
[45] May 3, 1977

[54] THIAALKYL PHENOLS

[75] Inventor: Hanns Lind, Liestal, Switzerland

[73] Assignee: Ciba-Geigy Corporation, Ardsley, N.Y.

[22] Filed: June 23, 1975

[21] Appl. No.: 589,657

Related U.S. Application Data

[63] Continuation of Ser. No. 394,957, Sept. 6, 1973, abandoned.

[52] U.S. Cl. .............................. 260/470; 252/406; 260/45.85 H; 260/516; 260/607 R; 260/607 A
[51] Int. Cl.² .................................... C07C 149/40
[58] Field of Search ...................... 260/470, 516

[56] References Cited

UNITED STATES PATENTS

| | | | |
|---|---|---|---|
| 3,546,272 | 12/1970 | Braus et al. | 260/470 |
| 3,637,802 | 1/1972 | Eggensperger et al. | 260/470 |
| 3,699,152 | 10/1972 | Hechenbleikner et al. | 260/470 |

OTHER PUBLICATIONS

Adams et al.; Organic Reactions, J. Wiley & Sons, New York, (1963), vol. 13, pp. 165–180.
Walling, Free Radicals in Solution, John Wiley, New York, (1957), pp. 312–321.

*Primary Examiner*—Howard T. Mars
*Attorney, Agent, or Firm*—Charles W. Vanecek; Nestor W. Shust

[57] ABSTRACT

New thiaalkylphenols are used as stabilizers for organic material. They are prepared by reacting corresponding alkenephenols with mercaptans.

5 Claims, No Drawings

THIAALKYL PHENOLS

This is a continuation of application Ser. No. 394,957, filed Sept. 6, 1973, and now abandoned.

The present invention relates to new compounds, the method for their manufacture, their use for stabilising organic material against thermo-oxidative degradation and the organic material stabilised with these new compounds.

The new compounds correspond to the general formula I

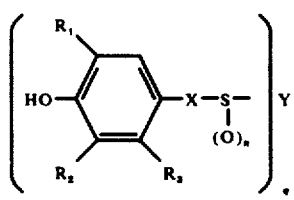

in which $R_1$ and $R_2$ independently of one another denote alkyl with 1 to 5 carbon atoms, cycloalkyl with 6 to 8 carbon atoms or aralkyl with 7 to 9 carbon atoms, $R_3$ denotes hydrogen or methyl, X denotes alkylene with 3 to 18 carbon atoms, with the phenol radical and the sulphur atom being separated by 2 or 3 carbon atoms, Y denotes alkyl with 1 to 18 carbon atoms, cycloalkyl with 5 to 8 carbon atoms, aralkyl with 7 to 9 carbon atoms, oxaalkyl with 3 to 21 carbon atoms, thiaalkyl with 3 to 21 carbon atoms, mercaptoalkyl with 2 to 18 carbon atoms, alkoxycarbonylalkyl with 3 to 21 carbon atoms, carboxyalkyl with 2 or 3 carbon atoms, hydroxyalkyl with 2 to 8 carbon atoms, acyloxyalkyl with 4 to 20 carbon atoms, alkylene with 2 to 18 carbon atoms, oxaalkylene with 4 to 18 carbon atoms, thiaalkylene with 4 to 18 carbon atoms, hydroxyalkylene with 3 to 21 carbon atoms, acyloxyalkylene with 5 to 23 carbon atoms, alkoxyalkylene with 4 to 22 carbon atoms or one of the groups

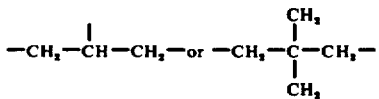

with hetero-atoms in the radical Y being separated from sulphur, or the sulphur atoms being separated from one another, by at least 2 carbon atoms, n denotes 0, 1 or 2 and q denotes 1, 2, 3 or 4.

It is known to employ thio compounds of sterically hindered phenols as stabilisers against thermo-oxidative degradation of polymers. However, these compounds suffer from the disadvantage that in practical use they can lead to undesired disolourations of the substrates.

It has now been found, surprisingly, that the compounds of the formula I are excellent stabilisers against the thermo-oxidative degradation of polymers.

As compared to similar previously known compounds, their advantage is that when used in practice, especially under the action of sunlight and industrial waste gases, so-called "gas fading conditions", they cause no discolouration whatsoever on the inherently colourless substrates; that is to say, the compounds according to the invention, of the formula I, show the technically desired combination of an excellent anti-oxidant action and colour stability of the polymers stabilised with these compounds.

In the definition of the compounds of the formula I, $R_1$, $R_2$ and/or Y can be alkyl groups. Within the limits indicated, they can be, for example, methyl, ethyl, iso-propyl, butyl, sec.-butyl, tert.-butyl, amyl, tert.-amyl, sec.-amyl, hexyl, octyl, tert.-octyl, decyl, dodecyl, tetradecyl or octadecyl.

$R_1$, $R_2$ and/or Y can also denote cycloalkyl groups which, within the indicated limits, are, for example, cyclohexyl, α-methylcyclohexyl or cyclooctyl.

$R_1$, $R_2$ and/or Y can also be aralkyl groups, such as benzyl, α-phenylethyl or α,α-dimethylbenzyl.

If the radicals X and Y in the definition of the formula I are an alkylene group, this can, within the indicated limits, be, for example, ethylene, propylene, trimethylene, tetramethylene, hexamethylene, octamethylene, decamethylene or octadecamethylene.

If Y denotes oxaalkyl with 3 to 21 carbon atoms it can be, for example, 3-oxtabutyl, 3-oxapentyl, 3-oxaheptyl, 3-oxapentadecyl or 3-oxaheneicosyl, whilst if it denotes thiaalkyl with 3 to 21 carbon atoms it can be, for example, 3-thiabutyl, 3-thiapentyl, 3-thiaheptyl, 3-thiaundecyl, 3-thiapentadecyl, 3-thianonadecyl and 3-thiaheneicosyl.

If Y is a mercaptoalkyl with 2 to 18 carbon atoms, it can be 2-mercaptoethyl, 3-mercaptopropyl, 12-mercaptoundecyl or or 18-mercaptooctadecyl.

If Y denotes alkoxycarbonylalkyl with 3 to 21 carbon atoms, it can denote methoxycarbonylmethyl, sec.-butoxycarbonylmethyl, 2-ethylhexoxycarbonylmethyl, dodecyloxycarbonylmenthyl, octadecyloxycarbonylmethyl, methoxycarbonylethyl, butoxycarbonylethyl, dodecyloxycarbonylethyl or octadecyloxycarbonylethyl.

Y as carboxyalkyl with 2 or 3 carbon atoms is carboxymethyl or carboxyethyl.

As hydroxyalkyl with 2 to 18 carbon atoms, Y is, for example, 2-hydroxyethyl, 3-hydroxypropyl, 12-hydroxyundecyl or 18-hydroxyoctadecyl.

If Y denotes acyloxyalkyl with 4 to 20 carbon atoms, "acyl" is, for example, the radical of an aliphatic or aromatic carboxylic acid with 2 to 18 carbon atoms, for example of an alkanoic acid such as acetic acid, propionic acid, caproic acid, lauric acid or stearic acid, or unsubstituted or substituted benzoic acid, such as benzoic acid, p-tert.butylbenzoic acid or p-tert. octylbenzoic acid. Acyloxyalkyl is, for example, 2-acetoxyethyl, 2-propionyloxyethyl, 2-capryloxyethyl, 2-lauryloxyethyl, 2-stearyloxyethyl, 3-acetoxypropyl, 3-propionyloxypropyl, 3-lauryloxypropyl, 3-capryloxypropyl, 3-stearyloxypropyl or 3-benzoyloxypropyl.

Y as oxaalkylene with 4to 18 carbon atoms can denote the divalent radical of 3-oxapentane, 3-oxaheptane, 3-oxaundecane or 3-oxapentadecane and Y as thiaalkylene with 4 to 18 carbon atoms can denote the divalent radical of 3-thiapentane, 3-thiaheptane, 3 thiaundecane, 3-thiapentadecane, 3-thianonadecane or 4-thiadecane.

If Y denotes hydroxyalkylene with 3 to 21 carbon atoms it is, for example, 2-hydroxytrimethylene or 3-hydroxytetramethylene.

If Y is acyloxyalkylene with 5 to 23 carbon atoms, acyl preferably denotes the radical of an aliphatic carboxylic acid such as of an alkanoic acid with 2 to 20 carbon atoms. Examples of such acids are acetic acid, propionic acid, carpoic acid, lauric acid, stearic acid or arachidic acid. Examples of acyloxyalkylene are 2- acetoxytrimethylene, 2-propionyloxytrimethylene or 3-stearoyloxytetramethylene.

If Y denotes alkoxyalkylene with 4 to 22 carbon atoms, it is, for example, 2-methoxytrimethylene, 2-dodecyloxytrimethylene, 3-dodecyloxytetramethylene or 3-octadecyloxytetramethylene, Amongst the compounds of the formula I, preferred compounds are those in which $R_1$ and $R_2$ independently of one another denote alkyl with 1 to 5 carbon atoms, $R_3$ denotes hydrogen or methyl, X denotes alkylene with 3 to 18 carbon atoms, the phenyl radical and the sulphur atom being separated by 2 or 3 carbon atoms, Y denotes alkyl with 1 to 18 carbon atoms, cycloalkyl with 5 to 7 carbon atoms, aralkyl with 7 to 9 carbon atoms, thiaalkyl with 3 or 4 carbon atoms, mercaptoalkyl with 2 to 18 carbon atoms, alkoxycarbonylalkyl with 3 to 21 carbon atoms, carboxyalkyl with 2 or 3 carbon atoms, hydroxyethyl, acyloxyethyl with 4-20 carbon atoms, ethylene with 2 to 18 carbon atoms or the

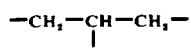

radical, with hetero-atoms in the radical Y being separated from sulphur by at least 2 carbon atoms, $n$ denotes 0, 1 or 2 and $q$ denotes 1, 2 or 3.

Particularly preferred compounds are those of the formula I in which $R_1$ and $R_2$ independently of one another denote alkyl with 1 to 4 carbon atoms, such as methyl or tert.-butyl, $R_3$ denotes hydrogen or methyl, preferably hydrogen, X denotes alkylene with 3 to 5 carbon atoms, with the phenol radical and the sulphur atom being separated by 2 or 3 carbon atoms, such as

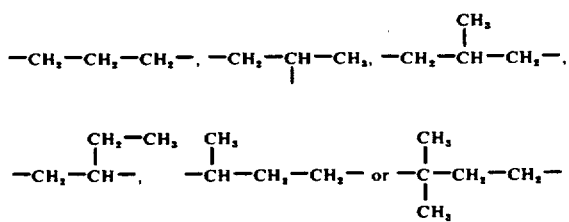

Y denotes alkyl with 8 to 18 carbon atoms, benzyl, propylene, mercaptoalkyl with 3 carbon atoms, 2-hydroxyethyl, alkoxycarbonylalkyl with 3 to 21 carbon atoms, carboxyalkyl with 2 or 3 carbon atoms or the

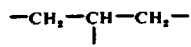

radical, with the hetero-atom in the radical Y being separated from sulphur by at least 2 carbon atoms, $n$ denotes 0, 1 or 2 and $q$ denotes 1, 2 or 3.

The compounds of the formula I, in which $n$ denotes 0, are manufactured by reaction of one mol of a compound of the formula II

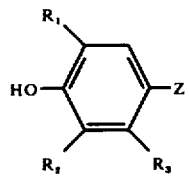

(II)

in which $R_1$, $R_2$ and $R_3$ are defined as under the formula I and Z denotes the radical of an alkene with 3 to 18 carbon atoms, the double bond in the alkene being either conjugated or in the allyl position relative to the phenyl nucleus, with one mol of a compound of the formula III

  (III)

in which Y and $q$ are under the formula I, at temperatures of 50°–160° C, in the presence of a radical-forming agent.

It is surprising that the phenols of the formula II can, under the conditions indicated, be reacted with mercapto compounds of the formula III though the radical-forming agents employed normally lead to the formation of stable aroxyls or secondary products thereof, for example isomerisation and disproportionation products.

Examples of radical-forming agents which can be used are di-tert.-butyl peroxide, dibenzoyl peroxide, tert.-butyl hydroperoxide, 1,1-bis[tert.-butylperoxy]-ethane, 2,2-bis-[tert.-butylperoxy]-butane, mesityl oxide peroxide, azo-bis-isobutyronitrile or the light from a source of UV radiation.

The compounds in which $n$ denotes 1 or 2 are manufactured by reacting compounds of the general formula I, with $n$ equal to 0, with an inorganic or organic oxidising agent in a solvent at temperatures of 0° – 100° C.

Examples of possible oxidising agents are: Hydrogen peroxide, per-acids such as peracetic acid or mono-perphthalic acid, or potassium persulphate.

Examples of solvents are glacial acetic acid, acetone, ether, acetic anhydride, methanol or mixtures of these solvents with water.

Examples of stabilisers of the formula I are: 2,6-Di-tert.-butyl-4-(4-thia-hexadecyl)-phenol, 2-methyl-6-tert.-butyl-4(4-thia-docosyl)phenol, 2,6-di-tert.-butyl-4-(4-thia-docosyl) phenol, 1,3-bis[(3-methyl-5-tert.-butyl-4-hydroxy-phenyl)4-thia-butyl]propane, 1,3-bis[(3,5-di-tert.-butyl-4-hydroxyphenyl)4-thia-butyl]-propane, 1,3-bis[(3,5-di-iso-propyl-4-hydroxy-phenyl)4-thia-butyl]propane, 1,2,3-tris[(3,5-di-tert.-butyl-4-hydroxy-phenyl)4-thia-butyl]propane, 1,2,3-tris[(3-methyl-5-tert.-butyl-4-hydroxy-phenyl)4-thia-butyl]propane, 1,2,3,4-tetra[(3,5-di-tert.-butyl-4-hydroxy-phenyl)4-thiapentyl]methane, 1,2,3,4-tetra[(3-methyl-5-tert.-butyl-4-hydroxy-phenyl)4-thia-pentyl]methane, 6-[3,5-di-tert.-butyl-4-hydroxy-phenyl]3-thia-caproic acid octadecyl ester, 6-[3-methyl-5-tert.-butyl-4-hydroxyphenyl]3-thia-caproic acid octadecyl ester, 7-[3-methyl-5-tert.-butyl-4-hydroxy-phenyl]4-thiaoenanthic acid octadecyl ester, 7-[3,5-di-tert.-butyl-4-hydroxyphenyl]4-thia-oenanthic acid octadecyl ester, 6-[3-methyl-5-tert.-butyl-4-hydroxy-phenyl]3-thia-hexyl stearate, 6-[3,5-di-tert.-butyl-4-hydroxyphenyl]3-thia-hexyl stearate, 6-(3,5-di-tert.-butyl-4-hydroxyphenyl)4-thia-caproic acid nitrile, 2,6-di-tert.-butyl-4(4,7-di-thia-nonadecyl)phenol, 2,6-di-tert.-butyl-4(4-thia-2-methyldocosyl)phenol, 1,3-bis[(3,5-di-tert.-butyl-4-hydroxy-phenyl)4-thia-2-methyl-butyl]propane, 1,2,3-tris[(3,5-di-tert.-butyl-4-hydroxy-phenyl)4-thia-2-methyl-butyl]propane, 1,2,3,4-tetra[(3,5-di-tert.-butyl-4-hydroxyphenyl)4-thia-2-methyl-pentyl]methane, 6-[3,5-di-tert.-butyl-4-hydroxyphenyl]-3-thia-5-methyl-caproic acid octadecyl ester, 7-[3,5-di-tert.-butyl-4-hydroxyphenyl]4-thia-6-methyl-oenanthic acid octadecyl ester, 6-[3,5-di-tert.-butyl-4-hydroxyphenyl]-3-thia-5-methyl-hexyl stearate, 3-(3,5-di-tert.-butyl4-hydroxyphenyl)-propyl-dodecyl-sulphone, 3-(3,5-di-tert.-butyl-4-hydroxyphenyl)-propyl-octadecyl-sulphone, 3-(3-methyl-5-tert.-butyl-4-hydroxyphenyl)-2-methyl propyl-octadecylsulphone, 3-(3,5-di-tert.-butyl-4-hydroxyphenyl)-propyl-carbooctadecyloxymethylsulphone, 3-(3,5-di-tert.-butyl-4-hydroxyphenyl)-2-methylpropyl-carbooctadecyloxymethylsulphone, 3-(3,5-di-tert.-butyl-4-hydroxyphenyl)propyl-carbooctadecyloxyethylsulphone and 3-(3,5-di-tert.-butyl-4-hydroxyphenyl)2-methyl-propylcarbooctadecyloxyethylsulphone.

The compounds of the formula I are used as stabilisers for organic substrates. As such it is possible to use, for example:

1. Polymers which are derived from hydrocarbons with single or double unsaturation, such as polyolefines, such as, for example, polyethylene, which can optionally be crosslinked, polypropylene, polyisobutylene, polymethylbutene-1, polymethylpentene-1, polybutene-1, polyisoprene, polybutadiene, polystyrene, polyisobutylene, copolymers of the monomers on which the homopolymers mentioned are based, such as ethylenepropylene copolymers, propylene-butene-1 copolymes, propylene-isobutylene copolymers, styrene-butadiene copolymers and terpolymers of ethylene and propylene with a diene, such as, for example, hexadiene, dicyclopentadiene or ethylidenenorbornen; mixtures of the abovementioned homopolymers, such as, for example, mixtures of polypropylene and polyethylene, polypropylene and polybutene-1, or polypropylene and polyisobutylene.

2. Vinyl polymers containing halogen, such as polyvinyl chloride, polyvinylidene chloride, polyvinyl fluoride, but also polychloroprene and chlorinated rubbers.

3. Polymers which are derived from α,β-unsaturated acids and their derivatives, such as polyacrylates and polymethacrylates, polyacrylamides and polyacrylonitrile, as well as their copolymers and other vinyl compounds, such as acrylonitrile/butadiene/styrene, acrylonitrile/styrene and acrylonirile/styrene/acrylic ester copolymers.

4. Polymers which are derived from unsaturated alcohols and amines or their acyl derivatives or acetals, such as polyvinyl alcohols, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene/vinyl acetate copolymers.

5. Homopolymers and copolymers which are derived from epoxides, such as polyethylene oxide or the polymers which are derived from bis-glycidyl ethers.

6. Polyacetals, such as polyoxymethylene and polyoxyethylene, as well as those polyoxymethylenes which contain ethylene oxide as the comonomer.

7. Polyphenylene oxides.

8. Polyurethanes and polyureas.

9. Polycarbonates.

10. Polysulphones.

11. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

12. Polyesters which are derived from dicarboxylic acids and dialcohols and/or from hydroxycarboxylic acids or the corresponding lactones, such as polyethylene glycol terephthalate or poly-1,4-dimethylolcyclohexane terephthalate.

13. Crosslinked polymers which are derived from aldehydes on the one hand and phenols, ureas and melamines on the other, such as phenol-formaldehyde, urea-formaldehyde and melamine-formaldehyde resins.

14. Alkyd resins, such as glycerine-phthalic acid resins and their mixtures with melamine-formaldehyde resins.

15. Unsaturated polyester resins which are derived from copolyesters of saturated and unsaturated dicarboxylic acids with polyhydric alcohols, with vinyl compounds as crosslinking agents, and also their halogen-containing modifications of low inflammability.

16. Natural polymers such as cellulose, rubber, proteins and their polymer-homologously chemically modified derivatives, such as cellulose acetates, cellulose propionates and cellulose butyrates, or the cellulose ethers, such as methylcellulose.

17. High molecular monomeric substances, for example mineral oils, animal and vegetable fats, oils and waxes, or oils, waxes and fats based on synthetic esters.

The compounds of the formula I are incorporated into the substrates in a concentration of 0.01 to 5% by weight calculated relative to the material to be stabilised.

Preferably, 0.05 to 2.0, and particularly preferentially 0.1 to 1.0,% by weight of the compounds, calculated relative to the material to be stabilised, are incorporated into the latter. The incorporation can take place before or during shaping, for example by mixing in at least one of the compounds of the formula I and optionally further additives according to the methods customary in the art, or by applying the dissolved or dispersed compounds to the polymer, if appropriate with subsequent evaporation of the solvent.

In the case of crosslinked polyethylene, the compounds are added before crosslinking.

The compounds of the formula I can also be added before or during polymerisation, and possible incorporation into the polymer chain results in stabilised substrates in which the stabilisers are not volatile or extractable.

As further additives together with which the stabilisers can be employed, there should be mentioned;

1. Antioxidants of the hydroxyaryl series, such as, for exmaple,

A. Simple 2,6-dialkylphenols such as, for example, 2,6-ditert.butyl-4-methylphenol, 2-tert.butyl-4,6-dimethylphenol, 2,6-ditert.butyl-4-methoxymethylphenol and 2,6-dioctadecyl-4-methylphenol.

B. Derivatives of alkylated hydroquinones such as, for example, 2,5-ditert.butyl-hydroquinone, 2,5-ditert.amyl-hydroquinone, 2,6-ditert.butyl-hydroquinone, 2,5-ditert.butyl-4-hydroxy-anisole, 3,5-ditert.butyl-4-hydroxy-anisole, tris-(3,5-ditert.butyl-4-hydroxyphenyl)-phosphite, 3,5-ditert.butyl-4-hydroxyphenyl-stearate and di-(3,5-ditert.butyl-4-hydroxyphenyl-adipate.

C. Hydroxylated thiodiphenyl ethers such as, for example, 2,2'-thiobis-(6-tert.butyl-4-methylphenol), 2,2'-thiobis-(4-octylphenol), 4,4'-thiobis-(6-tert.butyl-3-methylphenol), 4,4'-thiobis-(3,6-di-sec.amylphenol), 4,4'-thiobis-(6-tert.butyl-2-methylphenol) and 4,4'-bis(2,6-dimethyl-4-hydroxyphenyl)-disulphide.

D. Alkylidene-bisphenols such as, for example, 2,2'-methylene-bis-(6-tert.butyl-4-methylphenol),2,2'-methylene-bis-(6-tert.butyl-4-ethylphenol), 4,4'-methylene-bis-(6-tert.butyl-2-methylphenol), 4,4'-methylene-bis-(2,6-ditert.butylphenol), 2,6-di-(3-tert.butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)-butane, 1,1-bis-(5-tert.butyl-4-hydroxy-2-methylphenyl)-butane, 2,2-bis-(5-tert.butyl-4-hydroxy-2-methylphenyl)-butane, 2,2-bis-(3,5-di-tert.butyl-4-hydroxyphenyl)-propane, 1,1,3-tris-(5-tert.butyl-4-hydroxy-2-methylphenyl)-butane, 2,2-bis-(5-tert.butyl-4-hydroxy-2-methylphenyl)-4-n-dodecylmercapto-butane, 1,1,5,5-tetra-(5-tert.butyl-4-hydroxy-2-methylphenyl)-pentane and ethylene-glycol-bis-[3,3-bis-(3'-tert.butyl-4'-hydroxyphenyl)-butyrate].

E. O-, N- and S-benzyl compounds such as, for example, 3,5,3',5'-tetra-tert.butyl-4,4'-dihydroxydibenzyl ether, 4-hydroxy-3,5-dimethylbenzyl-mercaptoacetic acid octadecyl ester, tri-(3,5-di-tert.butyl-4-hydroxybenzyl)-amine and bis-(4-tert.butyl-3-hydroxy-2,6-dimethylbenzyl)-dithiol terephthalate.

F. Hydroxybenzylated malonic esters such as, for example, 2,2-bis-(3,5-di-tert.butyl-2-hydroxybenzyl)-malonic acid dioctecyl ester, 2-(3-tert.butyl-4-hydroxy-5-methylbenzyl)-malonic acid dioctadecyl ester, 2,2-bis-(3,5-ditert.butyl-4-hydroxybenzyl)-malonic acid didodecylmercapto ethylester and 2,2-bis-(3,5-ditert.butyl-4-hydroxybenzyl)malonic acid di-(4-tert.octyl-phenyl) ester.

G. Hydroxybenzyl-aromatics such as, for example, 1,3,5-tri-(3,5-ditert.butyl-4-hydroxybenzyl)-2,4,6-trimethylbenzene, 1,4-(3,5-ditert.butyl-4-hydroxybenzyl)-2,3,5,6-tetramethylbenzene and 2,4,6-tri-(3,5-ditert.butyl-4-hydroxybenzyl)-phenol. di-( H. s-Triazine compounds such as, for example, 2,4-bis-octylmercapto-6-(3,5-ditert.butyl-4-hydroxy-yanilino)-s-triazine, 2-octylmercapto-4,6-bis-(3,5-ditert.butyl-4-hydroxyanilino)-s-triazine, 2-octylmercapto-4,6-bis-(3,5-ditert.butyl-4-hydroxyphenoxy)-s-triazine, 2,4,6-tris-(3,5-ditert.butyl-4-hydroxyphenoxy)-s-triazine, 2,4,6-tris-(3,5-ditert.butyl-4-hydroxyphenylethyl)-s-triazine and 1,3,5-tris-(3,5-ditert.butyl-4-hydroxybenzyl)-isocyanurate.

I. Amides of 3,5-ditert.butyl-4-hydroxyphenylpropionic acid such as, for example, 1,3,3-tri-(3,5-ditert.butyl-4-hydroxyphenyl-propionyl)-hexahydro-s-triazine and N,N'-di-(3,5-ditert.butyl-4-hydroxyphenyl-propionyl)-hexamethylenediamine.

K. Esters of 3,5-ditert.butyl-4-hydroxyphenylpropionic acid with monohydric or polyhydric alcohols, such as, for example, methanol, ethanol, octadecanol; 1,6-hexanediol; 1,9-nonanediol, ethylene glycol; 1,2-propanediol, diethylene glycol, thiodiethylene glycol, neopentyl glycol, 3-thiaundecanol, 3-thiapentadecanol, trimethylhexanediol, trimethylolethane, trimethylolpropane, pentaerythritol, tris-hydroxyethyl-isocyanurate and 4-hydroxymethyl-1-phospha-2,6,7-trioxabicyclo[2,2,2]octane.

L. Esters of 5-tert.butyl-4-hydroxy-3-methylphenyl-propionic acid with monohydric or polyhydric alcohols such as, for example, methanol, ethanol, octadecanol; 1,6-hexanediol; 1,9-nonanediol, ethylene glycol; 1,2-propanediol, diethylene glycol, thiodiethylene glycol, neopentyl glycol, 3-thiaundecanol, 3-thia-pentadecanol, trimethylhexanediol, trimethylolethane, trimethylolpropane, pentaerythritol, trishydroxyethyl-isocyanurate and 4-hydroxymethyl-1-phospha-2,6,7-trioxa-bicyclo[2,2,2]octane.

M. Esters of 3,5-ditert.butyl-4-hydroxyphenylacetic acid with monohydric or polyhydric alcohols such as, for example, methanol, ethanol, octadecanol; 1,6-hexanediol; 1,9-nonanediol, ethylene glycol, 1,2-propanediol, diethylene glycol, thiodiethylene glycol, neopentyl glycol, 3-thiaundecanol, 3-thia-pentadecanol, trimethylhexanediol, trimethylolethane, trimethylolpropane, pentaerythritol, trishydroxyethylisocyanurate and 4-hydroxymethyl-1-phospha-2,6,7-trioxabicyclo[2,2,2]octane.

N Acylaminophenols such as, for example, N-(3,5-ditert.butyl-4-hydroxyphenyl)-stearic acid amide and N,N'-di-(3,5-ditert.butyl-4-hydroxyphenyl)-thi-obisacetamide.

O. Benzylphosphonates such as, for example, 3,5-ditert.butyl-4-hydroxybenzyl-phosphonic acid dimethyl ester, 3,5-di-tert.butyl-4-hydroxybenzyl-phosphonic acid diethyl ester, 3,5-ditert.butyl-4-hydroxybenzyl-phosphonic acid dioctadecyl ester and 5-tert.butyl-4-hydroxy-3-methylbenzyl-phosphonic acid diocadecyl ester.

2. Antioxidants of the aminoaryl series, above all aniline and naphtylamine derivatives as well as their heterocyclic derivatives, for example: Phenyl-1-naphthylamine, phennyl-2-naphthylamine, N,N'-diphenyl-p-phenylenediamine, N,N'-di-2-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2-dihydroquinoline, monooctyliminodibenzyl and dioctyliminodibenzyl and polymerised 2,2,4-trimethyl-1,2-dihydroquinoline.

2. UV absorbers and light protection agents, such as:
a. 2-(2'-Hydroxyphenyl)-benztriazoles, for example 2-(2'-hydroxy-5'-methylphenyl)-benztriazole, 2-(2'-hydroxy-3,5'-di-tert.butylphenyl)-benztriazole, 2(2'-hydroxy-5'-tert.butylphenyl)-benztriazole, 2-(2'-hydroxy-3,',5'-tert.butylphenyl)-5-chloro-benztriazole, 2-(2'-hydroxy-3'-sec.butyl-5'-tert.butylphenyl)-benztriazole, 2-(2'-hydroxy-3'-[α-methylbenzyl]-5'-methylphenyl)-benztriazole, 2-(2-hydroxy-3'-[α-methylbenzyl]5'-methylphenyl)-5-chloro-benztriazole, 2-(2'-hydroxy-4'-octoxyphenyl)-benztriazole, 2-(2'-hydroxy-3',5'-di-tert.amylphenyl)-benztriazole, 2(2'-hydroxy-3'-methyl-5'-carbomethoxyethylphenyl)-benztriazole, 2-(2'-hydroxy-3',5'-di-tert.amylphenyl)-5-chloro-benztriazole, 2-(2'-hydroxy-5'-[1,1,3,3-tetramethylbutyl]-phenyl)-benztriazole, 2-(2'-hydroxy-4'-hydroxyphenyl)-benztriazole and 2-(2'-hydroxy-4'-methoxyphenyl)-benztriazole.

b. 2,4-Bis-(2'-hydroxyphenyl)-6-alkyl-s-triazines, for example the 6-ethyl- or 6-undecyl-derivative.

c. 2-Hydroxy-benzophenones, for example the 4-hydroxy-, 4-methoxy-, 4-octoxy-, 4-dodecyloxy-, 4,2',-4'-trihydroxy- or 2'-hydroxy-4,4'-dimethoxy-derivative.

d. 1,3-Bis-(2'-hydroxy-benzoyl)-benzenes, for example 1,3-bis-(2'-hydroxy-4'-hexyloxy-benzoyl)-benzene, 1,3-bis-(2'-hydroxy-4'-octoxy-benzoyl)-benzene, and 1,3-bis-(2'-hydroxy-4'-dodecyloxy-benzoyl)-benzene.

e. Aryl esters of optionally substituted benzoic acids such as, for example, phenyl salicylate, octylphenyl salicylate, di-benzoylresorcinol, bis-(4-tert.butylbenzoyl)-resorcinol, benzoylresorcinol and 3,5-di-tert.butyl-4-hydroxybenzoic acid 2,4-di-tert.butyl-phenyl ester, octadecyl ester or 2-methyl-4,6-di-tert.butyl-phenyl ester.

f. Acrylates, for example α-cyano-ββ-diphenylacrylic acid ethyl ester or isooctyl ester, α-carbomethoxy-cinnamic acid methyl ester, α-cyano-β-methyl-p-methoxycinnamic acid methyl ester or butyl ester and N-(β-carbomethoxy-vinyl)-2-methyl-indoline.

g. Nickel compounds, for example nickel complexes of 2,2'-thiobis-(4-tert.octylphenol), such as the 1:1 and 1:2 complex, optionally with other ligands such as n-butylamine, nickel complexes of bis-(4-tert.octylphenyl)-sulphone, such as the 2:1 complex, optionally with other ligands such as 2-ethylcaproic acid, nickel dibutyldithiocarbamate, nickel salts of 4-hydroxy-3,5-di-tert.butylbenzyl-phosphonic acid monoalkyl esters, such as the methyl, ethyl or butyl ester, the nickel complex of 2-hydroxy-4-methyl-phenyl-undecylketoxime and nickel 3,5-ditert.butyl-4-hydroxy-benzoate.

h. Oxalic acid diamides, for example 4,4'-di-octyloxy oxanilide, 2,2'-di-octyloxy-5,5'-di-tert.butyl-oxanilide and 2,2'-di-dodecyloxy-5,5'-di-tert.butyl-oxanilide.

3. Metal deactivators, such as oxanilide, isophthalic acid dihydrazide, sebacic acid bis-phenylhydrazide, bis-benzylideneoxalic acid dihydrazide, N,N'-diacetyl-adipic acid dihydrazide, N,N'-bis-salicyloyl-oxalic acid dihydrazide, N,N'-bis-salicyloyl-hydrazine and N,N'-bis-(3,5-ditert.butyl-4-hydroxyphenyl-propionyl)-hydrazine.

4. Phosphites, such as triphenylphosphite, diphenylalkylphosphites, phenyldialkylphosphites, trinonylphenylphosphite, trilaurylphosphite, trioctadecylphosphite, 3,9-di-isodecyloxy-2,4,8,10-tetraoxa-3,9-diphosphaspiro-(5,5)-undecane and tri-(4-hydroxy-3,5-di-tert.butylphenyl)-phosphite.

5. Compounds which destroy peroxides, such as esters of β-thiodipropionic acid, for example the lauryl, stearyl, myrystyl or tridecyl esters, salts of 2-mercaptobenzimidazole, for example the zinc salt, and diphenylthiourea for polyolefines.

6. Polyamide stabilisers, such as copper salts in combination with iodides and/or further phosphorus compounds and salts of divalent manganese.

7. Basic co-stabilisers, such as polyvinyl pyrrolidone, melamine, benzoguanamine, triallyl-cyanurate, dicyandiamide, urea derivatives, hydrazine derivatives, amines, polyamides, polyurethanes, and alkali metal salts and alkaline earth metal salts of higher saturated or unsaturated fatty acids such as, for example, Ca stearate.

8. PVC stabilisers such as organic tin compounds, organic lead compounds and Ba/Cd salts of fatty acids.

9. Nucleating agents, such as 4-tert.butylbenzoic acid, adipic acid and diphenylacetic acid.

10. Other additives such as plasticisers, lubricants for example glycerine monostearate, emulsifiers, antistatic agents, flameproofing agents, pigments, carbon black, asbestos, glass fibres, kaolin and talc.

The invention is explained in more detail in the examples which follow. Per cent (%) in the examples denotes per cent by weight and parts in the examples denote parts by weight.

EXAMPLE 1

Manufacture of

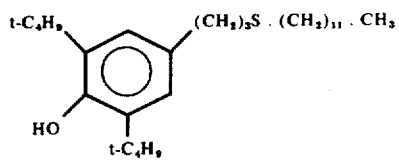

49.2 g (0.20 mol) of 4-allyl-2,6-di-tert.-butylphenol, 60.6 g (0.30 mol) of n-dodecylmercaptan and 2 g of azo-isobutyronitrile are together heated under a nitrogen atmosphere to 115° - 120° C, whilst stirring. The reaction is stopped after 6 hours.

Distillation of the reaction mixture yields crude 2,6-di-tert.butyl-4(4-thia-hexadecyl)phenol of boiling point $_{0.01}$: 210° - 220° C as a slightly yellowish oil which after chromatographic purification on a silica gel column and crystallisation from methanol is in the form of colourless crystals of melting point 26° - 27° C (stabiliser No. 1).

EXAMPLE 2

The procedure in Example 1 is followed, but the starting products are so chosen that the compounds 2.1 - 2.21 which are obtained correspond to the formulae listed in Table 1 below.

Table 1

| No. | Formula | Boiling point/melting point (° C) |
|---|---|---|
| 2.1 | H₃C, (CH₂)₃S—(CH₂)₇CH₃ / HO, H₃C | B.p.:₀.₀₁: 140–144 M.p.:25–27 |
| 2.2 | t-C₄H₉, (CH₂)₃S·CH₂·C₆H₅ / HO, t-C₄H₉ | B.p.₀.₁₁: 195–196 |
| 2.3 | [t-C₄H₉, (CH₂)₃SCH₂ / HO, t-C₄H₉]₂ CH₂ | B.p.: Chromatographed on SiO₂; colourless, Viscous oil |
| 2.4 | t-C₄H₉, (CH₂)₃S·(CH₂)₃SH / HO, t-C₄H₉ | B.p.₀.₀₃: 189–192 |
| 2.5 | t-C₄H₉, (CH₂)₃S(CH₂)₂OH / HO, t-C₄H₉ | B.p.₀.₁₅: 164–165 |
| 2.6 | t-C₄H₉, (CH₂)₃S·CH₂COOCH₃ / HO, t-C₄H₉ | B.p.₀.₂: 180–182 |
| 2.7 | t-C₄H₉, (CH₂)₃S·CH₂COOC₁₈H₃₇ / HO, t-C₄H₉ | Molecularly distilled at 210° C/0.001 mm Hg; slightly yellowish, viscous oil |

Table 1-continued

| No. | Formula | Boiling point/ melting point (° C) |
|---|---|---|
| 2.8 | t-C₄H₉—[HO, CH₃-phenyl]—(CH₂)₃S·CH₂COOCH₃ | B.p.₀.₅: 198–200 |
| 2.9 | t-C₄H₉—[HO, t-C₄H₉-phenyl]—(CH₂)₃S·(CH₂)₂COOC₁₆H₃₇ | B.p.:- Chromatographed on SiO₂; colourless, viscous, oil |
| 2.10 | t-C₄H₉—[HO, t-C₄H₉-phenyl]—(CH₂)₃S·CH₂COOH | B.p.₀.₁₃: 205–206 |
| 2.11 | H₃C—[HO, t-C₄H₉-phenyl]—(CH₂)₃S·CH₂COOH | B.p.₀.₁₆: 198–200 M.p.:69–69.5 |
| 2.12 | t-C₄H₉—[HO, t-C₄H₉-phenyl]—(CH₂)₃S·(CH₂)₂COOH | B.p.₀.₁: 200–03° M.p.:94–95 |
| 2.13 | t-C₄H₉—[HO, t-C₄H₉-phenyl]—(CH₂)₃S·(CH₂)₂OCOCH₃ | B.p.₀.₃: 196–97 |
| 2.14 | t-C₄H₉—[HO, t-C₄H₉-phenyl]—(CH₂)₃S·(CH₂)₂OCOC₁₇H₃₅ | M.p. 43–44 |
| 2.15 | t-C₄H₉—[HO, t-C₄H₉-phenyl]—(CH₂)₃S·(CH₂)₁₇·CH₃ | M.p. 49–50 |

The following compounds can be manufactured in the same manner:

2.16  6-(3,5-Di-tert.-butyl-4-hydroxyphenyl)-4-thiacaproic acid nitrile
2.17  6-(3-Methyl-5-tert.-butyl-4-hydroxyphenyl)-4-thiacaproic acid nitrile
2.18  2,6-Di-tert-butyl-4-(4,7-di-thia-pentadecyl)-phenol
2.19  2,6-Di-tert.-butyl-4-(4,7-di-thia-nonadecyl)-phenol
2.20  2,6-Di-tert.-butyl-4-(4-thia-7-oxa-undecyl)-phenol
2.21  2,6-Di-tert.-butyl-4-(4-thia-4-cyclohexyl-butyl)-phenol

EXAMPLE 3

Manufacture of

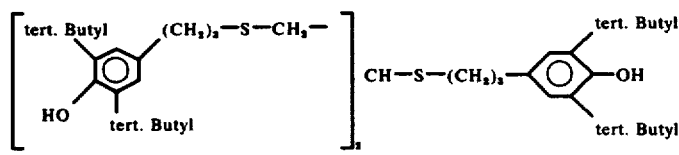

A mixture of 73.8 g (0.3 mol) of 4-allyl-2,6-ditert.-butylphenol, 11.6 g (0.083 mol) of 1,2,3-propanetri-thiol and 1.5 g of di-tert.-butyl peroxide is stirred for 12 hours at 120° –125° C under a nitrogen atmosphere. After cooling, the reaction mixture is kept for 2 hours under a vacuum of 0.1 mm Hg at 160° C and the residue is purified chromatographically on a silica gel column. 1,2,3-Tris[(3,5-di-tert.-butyl-4-hydroxyphenyl)4-thia-butyl]propane is obtained as an almost colourless viscous oil of which the structure was examined by ¹H-NMR spectroscopy. (Stabiliser No. 3).

EXAMPLE 4

Manufacture of

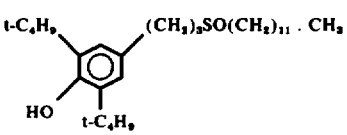

2.2 ml of 30% strength hydrogen peroxide are added to a solution of 9 g (0.02 mol) of 2,6-di-tert.-butyl-4-(4-thiahexadecyl)phenol in 15 ml of acetone and after standing for two days at room temperature, the solution is evaporated in vacuo. Crude 3-(3,5-di-tert.-butyl-4-hydroxy-phenyl)propyldodecyl]sulphoxide is obtained as a colourless oil which after chromatographic purification on a silica gel column and crystallisation from acetone gives colourless crystals of melting point 73° –74° C. (Stabiliser No. 4).

EXAMPLE 5

Manufacture of

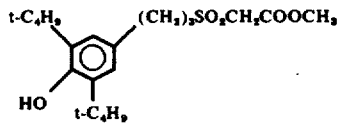

25.6 ml of 30% strength hydrogen peroxide are added to a solution of 30 g (0.085 mol) of 6-(3,5-di-tert.-butyl-4-hydroxyphenyl)-3-thia-caproic acid methyl ester in 210 ml of glacial acetic acid whilst cooling with ice, and after standing for three days at room temperature the reaction solution is poured onto ice. The oil which has precipiated is taken up in methylene chloride, the organic phase is successively extracted with 5% strength aqueous sodium bicarbonate solution and water and after drying over sodium sulphate the solvent is evaporated. Crude 3-(3,5-di-tert.-butyl-4-hydroxyphenyl)-propyl-carbomethoxymethyl-sulphone is obtained, which, when crystallised from methanol/water, is in the form of colourless crystals of melting point 68° – 69° C. (Stabiliser No. 5.)

EXAMPLE 6

The procedure of Example 5 is followed but the starting compounds are so chosen that the compounds 6.1 to 6.5 which are obtained correspond to the formulae listed in Table 2.

Table 2

| No. | Formula | Melting point, °C |
|---|---|---|
| 6.1 | H₃C—[3,5-positions], HO, CH₃ aromatic with (CH₂)₃SO₂·(CH₂)₈·CH₃ | 63 – 64 |
| 6.2 | t-C₄H₉, HO, t-C₄H₉ aromatic with (CH₂)₃SO₂(CH₂)₁₁·CH₃ | 61 – 62 |
| 6.3 | t-C₄H₉, HO, t-C₄H₉ aromatic with (CH₂)₃SO₂·CH₂COOC₁₈H₃₇ | 47.5 – 49 |
| 6.4 | t-C₄H₉, HO, t-C₄H₉ aromatic with (CH₂)₃SO₂·CH₂C₆H₅ | 148 – 149 |
| 6.5 | t-C₄H₉, HO, t-C₄H₉ aromatic with (CH₂)₃SO₂(CH₂)₂COOC₁₈H₃₇ | 48 – 49 |

EXAMPLE 7

Manufacture of

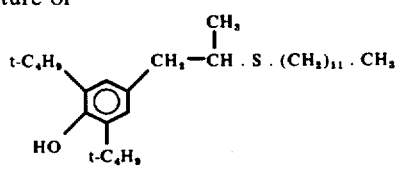

t-C₄H₉, HO, t-C₄H₉ aromatic with CH₂—CH(CH₃)·S·(CH₂)₁₁·CH₃

8.23 g (0.034 mol) of 4-(1-propenyl)-2,6-di-tert.-butyl-phenol of boiling point$_{12}$: 161°–165° C, manufactured from 4-allyl-2,6-di-tert.-butylphenol, in accordance with the instructions in J. Org. Chem. 29, 3014 (1964), 10.20 g (0.050 mol) of n-dodecylmercaptan and 1.2 g of bis-azo-isobutyronitrile are together stirred for 10 hours under nitrogen at 115°–120° C. Thereafter the reaction mixture is distilled in vacuo. 2,6-Di-tert.-butyl-4-(3-thia-2-methylpentadecyl)phenol of boiling point$_{0.06}$: 197°–200° C is obtained as a slightly yellowish, viscous oil of which the ¹H-NMR data and mass-spectroscopic data agree with the structure indicated. (Stabiliser No. 7).

EXAMPLE 8

The procedure under Example 1 is followed, the starting products being so chosen that the resulting compounds 8.1 – 8.5 correspond to the formulae listed in Table 3 below; the starting products listed in Table 4 are obtained analogously to the reaction for 4-allyl-2,6-di-tert.-butylphenol in U.S. Pat. No. 3,526,668.

Table 3

| No. | Formula | Boiling point (° C) |
|---|---|---|
| 8.1 | t-C₄H₉, HO, t-C₄H₉ aromatic with C(CH₃)₂—CH₂·CH₂·S·CH₂COOCH₃ | 175–176/ 0.33 mm Hg |
| 8.2 | t-C₄H₉, HO, t-C₄H₉ aromatic with CH(CH₃)·CH₂·S·CH₂·COOCH₃ | 160–165/ 0.08 mm Hg |
| 8.3 | t-C₄H₉, HO, t-C₄H₉ aromatic with CH(CH₂CH₃)·S·CH₂·COOCH₃ | 170–173/ 0.07 mm Hg |
| 8.4 | t-C₄H₉, HO, t-C₄H₉ aromatic with CH(CH₃)·CH₂·CH₂·S·CH₂·COOCH₃ | 177–179/ 0.1 mm Hg |
| 8.5 | t-C₄H₉, HO, t-C₄H₉, CH₃, CH₃ aromatic with (CH₂)₃SCH₂COOC₁₈H₃₇ | Molecularly distilled at 225° C/0.001 mm Hg; viscous oil |

Table 4

| Starting product for Example No. | Formula | Melting point/ boiling point (° C) |
|---|---|---|
| 8.1 | t-C₄H₉, HO, t-C₄H₉ aromatic with C(CH₃)₂·CH=CH₂ | M.p. 67–68 |
| 8.2 | t-C₄H₉, HO, t-C₄H₉ aromatic with CH(CH₃)·C=CH₂ | B.p.$_{10}$: 162–163 |
| 8.3 | t-C₄H₉, HO, t-C₄H₉ aromatic with CH₂·CH=CH—CH₃ | B.p.$_{10}$: 167–168 |
| 8.4 | t-C₄H₉, HO, t-C₄H₉ aromatic with CH(CH₃)·CH=CH₂ | B.p.$_{4}$: 117–120 |
| 8.5 | t-C₄H₉, HO, CH₃, CH₃ aromatic with CH₂—CH=CH₂ | B.p.$_{12}$: 163–65° |

EXAMPLE 9

The additives listed in Table 5 are sprinkled dry in a concentration of 0.5% onto dried polyamide 6 granules (relative viscosity = 2.9, 1% strength in concentrated sulphuric acid) and the sprinkle-coated mixtures are regranulated on a single-screw extruder at 260° C. 0.3 mm pressed films are then manufactured from the granules, again at 260° C, and 1 cm wide test strips are punched from these pressed films.

The effectiveness of the additives added to the test specimens is tested by heat aging in a circulating air oven at 165° C. The thermo-oxidative degradation of the material during heat aging is followed by periodically measuring the relative viscosity of a 1% strength solution in 96% strength sulphuric acid, and determining the time at which the relative viscosity has decreased from 2.9 to a value of 2.0.

Table 5

| Stabiliser Example No. | Heat aging time at 165° C for the solution viscosity $\eta_{rel}$ to decrease from 2.9 to 2.0, in hours |
|---|---|
| None | 9 |
| 1 | 48 |

EXAMPLE 10

100 parts of polypropylene (melt index 3.2 g/10 minutes, 230° C/2,160 g) are thoroughly mixed for 10 minutes in a shaking apparatus with 0.2 part of an additive listed in Table 6 below. The resulting mixture is kneaded for 10 minutes in a Brabender plastograph at 200° C and the mass thus obtained is subsequently pressed in a sheet press at 260° C platen temperature to give 1 mm thick sheets from which strips 1 cm wide and 17 cm long are punched.

The activity of the additives added to the test strips is tested by heat aging in a circulating air oven at 135° C and 149° C, with an additive-free test strip serving for comparison. 3 test strips of each formulation are employed. The incipient, easily visible decomposition of the test strip is defined as the end point.

Table 6

| Stabiliser Example No. | Days to reach incipient decomposition | |
|---|---|---|
| | 149° C | 135° C |
| None | 1 | 5 |
| 2.3 | 30 | 131 |
| 2.7 | 37 | 132 |
| 2.9 | 40 | 150 |
| 3 | 38 | 149 |

EXAMPLE 11

100 parts of polypropylene (melt index 3.2 g/10 minutes, 230° C/2,160 g) are thoroughly mixed for 10 minutes in a shaking apparatus with 0.1 part of one of the additives listed in Table 7 below and 0.3 part of dilauryl thiodipropionate.

The resulting mixture is kneaded for 10 minutes in a Brabender plastograph at 200° C and the composition thus obtained is subsequently pressed in a sheet press at 260° platen temperature to give 1 mm thick sheets from which strips 1 cm wide and 17 cm long are punched.

The activity of the additives added to the test strips is tested by heat aging in a circulating air oven at 135° C and 149° C, with a test strip which only contains 0.3 part of dilauroyl thiodipropionate serving for comparison. Three test strips of each formulation are tested. The incipient, easily visible decomposition of the test strip is defined as the end point.

Table 7

| Stabiliser Example No. | Days to reach incipient decomposition | |
|---|---|---|
| | 149° C | 135° C |
| None | 5 | 11 |
| 2.3 | 33 | 144 |
| 2.7 | 38 | 154 |
| 2.14 | 27 | 135 |
| 6.2 | 16 | 115 |

EXAMPLE 12

The test specimens described in Example 10 were additionally tested for their colour stability, in particular:

a. After incorporation (Table 8, column 2)

b. After 500 hours' exposure in a xenotest apparatus of Messrs. Hanau (Table 8, column 3)

c. After 1 week's treatment with boiling water (Table 8, column 4)

An empirical colour scale was used for Table 8, in which 5 denotes colourless, 4 denotes a just perceptible slight discolouration and 3, 2, 1 and 21 denote progressively stronger discolouration.

Table 8

| Stabiliser, Example No. | Colour assessment on scale 1 – 5 | | |
|---|---|---|---|
| | After incorporation | After exposure | Boiling water, 1 week |
| 2.3 | 4 | 4–5 | 4–5 |
| 2.7 | 4 | 4–5 | 4–5 |
| 2.9 | 4 | 4 | 4 |

EXAMPLE 13

100 parts of polypropylene (melt index 19 g/10 minutes; 230° C/2,160 g) are thoroughly mixed for 10 minutes in a shaking apparatus with 0.1 part of one of the additives listed in Table 9.

The resulting mixture is extruded in a laboratory single-screw extruder ("Plamvo") at 260° C nozzle temperature, 100 revolutions/minute, with a throughput of 50 g/minute, and is subsequently granulated.

The resulting granules are spun in a spinning apparatus at a nozzle temperature of 280° C to give multi-filaments which are subsequently stretched in the ratio of 1:5.5.

The resulting filaments are subjected to a "gas-fading test" based on Standard AATCC, Test Method 23–1957, which consists of exposing the test specimens to the waste gases from a butane gas burner at 60° C for 24 hours.

The visual assessment of the colour in both cases shows that the test specimens have remained colourless.

Table 9

| Stabiliser, Example No. | Visual assessment of colour |
|---|---|
| None | Colourless |
| Octadecyl-3-(3,5-di-tert.-butyl-4-hydroxy-phenyl)-propionate | Yellow |
| 2.3 | Colourless |
| 4 | Colourless |

EXAMPLE 14

Shavings (slices) 25 μ thick are cut by means of a microtome from the 1 mm thick test sheets described in Example 10. These slices are clamped between grids of stainless steel and the sample carrier thus obtained is suspended in a circulating air oven and aged at 135° C or 147° C. The time after which, on gently tapping the grids, degraded polypropylene drops out in the form of a powder is defined as the end point. (A check is carried out 1 – 2 × daily). The results are quoted in hours and are summarised in Table 10.

Table 10

| Stabiliser Example No. | Hours to incipient decomposition 147° C | 135° C |
|---|---|---|
| None | <10 | <20 |
| 2.3 | 140 | 400 |
| 2.7 | 120 | 310 |

What we claim is:
1. A compound of the formula

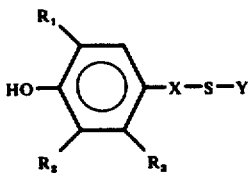

Wherein $R_1$ and $R_2$ are tert-butyl, $R_3$ is hydrogen or methyl, X is alkylene with 3 to 18 carbon atoms, with the phenol radical and the sulphur atom being separated by 2 or 3 carbon atoms and Y is alkoxy carbonylalkyl with 3 to 21 carbon atoms or carboxyalkyl with 2 or 3 carbon atoms.

2. A compound according to claim 1, wherein X is alkylene with 3 to 5 carbon atoms.

3. A compound according to claim 1, wherein $R_3$ is hydrogen, X is a group selected from $$-CH_2-CH_2-CH_2-, \quad -CH_2-\underset{CH_3}{\underset{|}{CH}}-CH_2, \quad -CH_2\underset{CH_3}{\underset{|}{CH}}-CH_2-,$$

$$-CH_2-\underset{\underset{CH_2-CH_3}{|}}{CH}-, \quad -\underset{\underset{CH_3}{|}}{CH}-CH_2-CH_2 \text{ and } -\underset{\underset{CH_3}{|}}{\overset{\overset{CH_3}{|}}{C}}-CH_2-CH_2-$$

4. The compound according to claim 1, of the formula

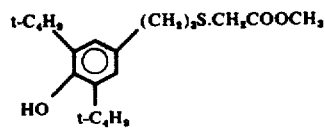

5. The compound according to claim 1, of the formula

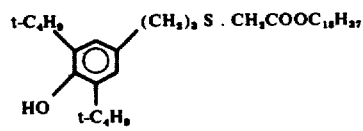

* * * * *